(12) United States Patent
Sheeran et al.

(10) Patent No.: US 12,213,836 B2
(45) Date of Patent: Feb. 4, 2025

(54) METHODS AND SYSTEMS FOR SEGMENTATION AND RENDERING OF INVERTED DATA

(71) Applicant: KONINKLIJKE PHILIPS N.V., Eindhoven (NL)

(72) Inventors: Paul Sheeran, Woodinville, WA (US); Thanasis Loupas, Kirkland, WA (US); Charles Tremblay-Darveau, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 645 days.

(21) Appl. No.: 17/431,491

(22) PCT Filed: Feb. 21, 2020

(86) PCT No.: PCT/EP2020/054631
§ 371 (c)(1),
(2) Date: Aug. 17, 2021

(87) PCT Pub. No.: WO2020/169805
PCT Pub. Date: Aug. 27, 2020

(65) Prior Publication Data
US 2022/0133278 A1    May 5, 2022

Related U.S. Application Data
(60) Provisional application No. 62/808,572, filed on Feb. 21, 2019.

(51) Int. Cl.
*A61B 8/08*     (2006.01)
*G06N 7/02*     (2006.01)
*G06T 15/08*    (2011.01)

(52) U.S. Cl.
CPC ............ *A61B 8/483* (2013.01); *A61B 8/0866* (2013.01); *A61B 8/5269* (2013.01); *G06N 7/02* (2013.01); *G06T 15/08* (2013.01)

(58) Field of Classification Search
CPC ..... A61B 8/483; A61B 8/0866; A61B 8/5269; G06N 7/02; G06T 15/08; G06T 5/70;
(Continued)

(56) References Cited

U.S. PATENT DOCUMENTS 6,443,896 B1    9/2002  Detmer
6,530,885 B1    3/2003  Entrekin et al.
(Continued)

FOREIGN PATENT DOCUMENTS

EP      2272434 A1       1/2011
JP      2004287603 A    10/2004
(Continued)

OTHER PUBLICATIONS

PCT/EP2020/054631 ISR & Written Opinion, Feb. 21, 2020, 15 Page Document.
(Continued)

*Primary Examiner* — Dhaval V Patel

(57) ABSTRACT

Systems and methods for preprocessing three dimensional (3D) data prior to generating inverted renders are disclosed herein. The preprocessing may include segmenting the 3D data to remove portions of the data associated with noise such that those portions do not appear in the generated render. The segmentation may include applying a mask to the 3D data. The mask may be generated by sorting data points in the 3D data set into a first set or a second set. In some examples, the 3D data may be filtered prior to generating the mask. In some examples, the mask may be adjusted
(Continued)

based on feature recognition. The preprocessing may allow the visualization of hypoechoic regions of interest in a volume.

13 Claims, 8 Drawing Sheets

(58) Field of Classification Search
CPC . G06T 7/136; G06T 2207/10136; G06T 7/11; G06T 19/00; G06T 2210/41
See application file for complete search history.

(56) References Cited

U.S. PATENT DOCUMENTS

| | | | |
|---|---|---|---|
| 11,497,557 B2* | 11/2022 | Haslam | G06T 7/0012 |
| 2005/0273009 A1 | 12/2005 | Deischinger et al. | |
| 2006/0171578 A1 | 8/2006 | Novak | |
| 2010/0099991 A1* | 4/2010 | Snyder | A61B 8/483 348/46 |
| 2016/0199036 A1* | 7/2016 | Pelissier | A61B 8/523 600/440 |
| 2018/0144471 A1* | 5/2018 | Govindjee | A61B 5/7282 |
| 2019/0114532 A1* | 4/2019 | Sunwoo | G06N 3/082 |
| 2019/0130188 A1* | 5/2019 | Zhou | G06T 7/248 |
| 2020/0372658 A1* | 11/2020 | De Winde | G06T 7/11 |

FOREIGN PATENT DOCUMENTS

| | | |
|---|---|---|
| WO | 2014168500 A1 | 10/2014 |
| WO | 2019145188 A1 | 8/2019 |

OTHER PUBLICATIONS

Krucker et al: 3D Spatial Compounding of Ultrasound Images Using Image-Based Nonrigid Registration; Ultrasound in Med. & Biol., vol. 26, No. 9, pp. 1475-1488, 2000.

Nagy: "3D/4D Volumetry in the Second and Third Trimester of Pregnancy"; Donald School Journal of Ultrasound in Obstetrics and Gynecology, Apr.-Jun. 2009, 3(2), pp. 18-24.

* cited by examiner

METHODS AND SYSTEMS FOR SEGMENTATION AND RENDERING OF INVERTED DATA

CROSS-REFERENCE TO PRIOR APPLICATIONS

This application is the U.S. National Phase application under 35 U.S.C. § 371 of International Application No. PCT/EP2020/054631, filed on Feb. 21, 2020, which claims the benefit of U.S. Provisional Patent Application No. 62/808,572, filed on Feb. 21, 2019. These applications are hereby incorporated by reference herein.

TECHNICAL FIELD

This application relates to inverted rendering of three-dimensional data. More specifically, this application relates to preprocessing of three-dimensional data prior to inverted rendering of the data.

BACKGROUND

Ultrasound images are generated by transmitting ultrasound signals into a subject (e.g., a patient) and processing the received echoes from the transmitted signals. In medical imaging, echoes are typically generated by tissue structures (e.g., cell walls, connective fibers) reflecting the ultrasound signal. The ultrasound signals may be transmitted through and echoes received from a volume to generate (e.g., render) a three-dimensional (3D) image of the volume. For example, in medical imaging, a 3D image of an organ (e.g., heart, liver) or a portion of an organ may be generated. The 3D image may be in color or grayscale where the color and/or lightness of a voxel corresponds to the intensity of the echo signal at that location. Typically, the 3D image in medical imaging is a "positive render." That is, voxels with the highest intensity signals are rendered with the lightest value (e.g., white in grayscale) and the voxels with the lowest intensity signals are rendered with the darkest value (e.g., black in grayscale). Positive rendering tends to highlight acoustically reflective structures while areas of low signal are de-emphasized.

Certain features in the volume may be of interest despite providing little or no echo signals (e.g., hypoechoic). For example, blood vessels, gall bladder, and some lesions may be rendered as dark areas in a 3D image of a subject's anatomy. An ultrasound system may generate a negative or "inverted render" of the 3D image. In an inverted render, voxels with the highest intensity signals are rendered with the darkest value (e.g., black in gray scale) and the lowest intensity signals are rendered with the lightest value (e.g., white in gray scale). Inverted renders may allow a user to more easily observe hypoechoic regions of interest. However, areas of low signal that do not contain features of interest (e.g., poorly coupled tissue, regions obscured by shadowing, noise) are also hypoechoic and may be emphasized in an inverted render. In some cases, the areas of low signal may so dominate the inverted render, the hypoechoic regions of interest are obscured. This may reduce or eliminate the utility of the inverted render.

SUMMARY

Methods and systems for preprocessing three dimensional (3D) data prior to generating an inverted render are described. Preprocessing the 3D data may include segmenting the 3D data into two or more sets, for example, data to be rendered and data not allowed to contribute to the 3D rendered image. Segmentation may be performed by applying a mask to the 3D data set. In some examples, the mask is a binary mask (e.g., the data points are sorted into two sets). Preprocessing may include reducing noise prior to segmentation. Reducing noise may include applying a smoothing kernel and/or an adaptive smoothing (e.g., persistence) algorithm. Reducing noise may improve the performance of the segmentation in some applications. Preprocessing the 3D data prior to generating an inverted render may reduce the obscuring of hypoechoic regions of interest by noise in some applications.

In accordance with at least one example disclosed herein, a method may include sorting data points of a three dimensional (3D) dataset into one of a first set or a second set, wherein the 3D dataset defines a first volume, generating a mask corresponding to the 3D dataset, wherein data points of the mask corresponding to data points of the 3D dataset sorted into the first set are set to a first value and data points of the mask corresponding to data points of the 3D dataset sorted into the second set are set to a second value, wherein an outer boundary of the data points of the mask set to the first value defines a second volume within the first volume, applying the mask to the 3D dataset such that data points of the 3D dataset corresponding to data points outside the second volume are discarded to generate a subset of the 3D dataset, and generating an inverted render from the subset of the 3D dataset.

In accordance with at least one example disclosed herein, a system may include a non-transitory computer readable medium including a three dimensional (3D) dataset defining a volume, and a processor configured to: sort data points of the 3D dataset into one of a first set or a second set, generate a mask corresponding to the 3D dataset, wherein data points of the mask corresponding to data points of the 3D dataset sorted into the first set are set to a first value and data points of the mask corresponding to data points of the 3D dataset sorted into the second set are set to a second value, determine an outer boundary of the data points of the mask set to the first value, define a second volume within the first volume based on the outer boundary, apply the mask to the 3D dataset to discard data points of the 3D dataset corresponding to data points outside the second volume to generate a subset of the 3D dataset, and generate an inverted render from the subset of the 3D dataset.

DESCRIPTION

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

As previously described, positive rendering of three dimensional (3D) datasets render (e.g., visualize) voxels associated with high intensity echo signals as bright or light values (e.g., white) while voxels associated with low intensity echo signals are visualized as dark values (e.g., black). In general, positive renderings that seek to bring out the brightest structures (e.g., most acoustically reflective) in a region of interest generally work as intended through the utilization of opacity maps and optimization control based on expected acoustic characteristics of commonly imaged objects, for example, tissues and/or organs interrogated via ultrasound. Opacity maps and optimization controls are included on many current ultrasound imaging systems.

Figure 1:
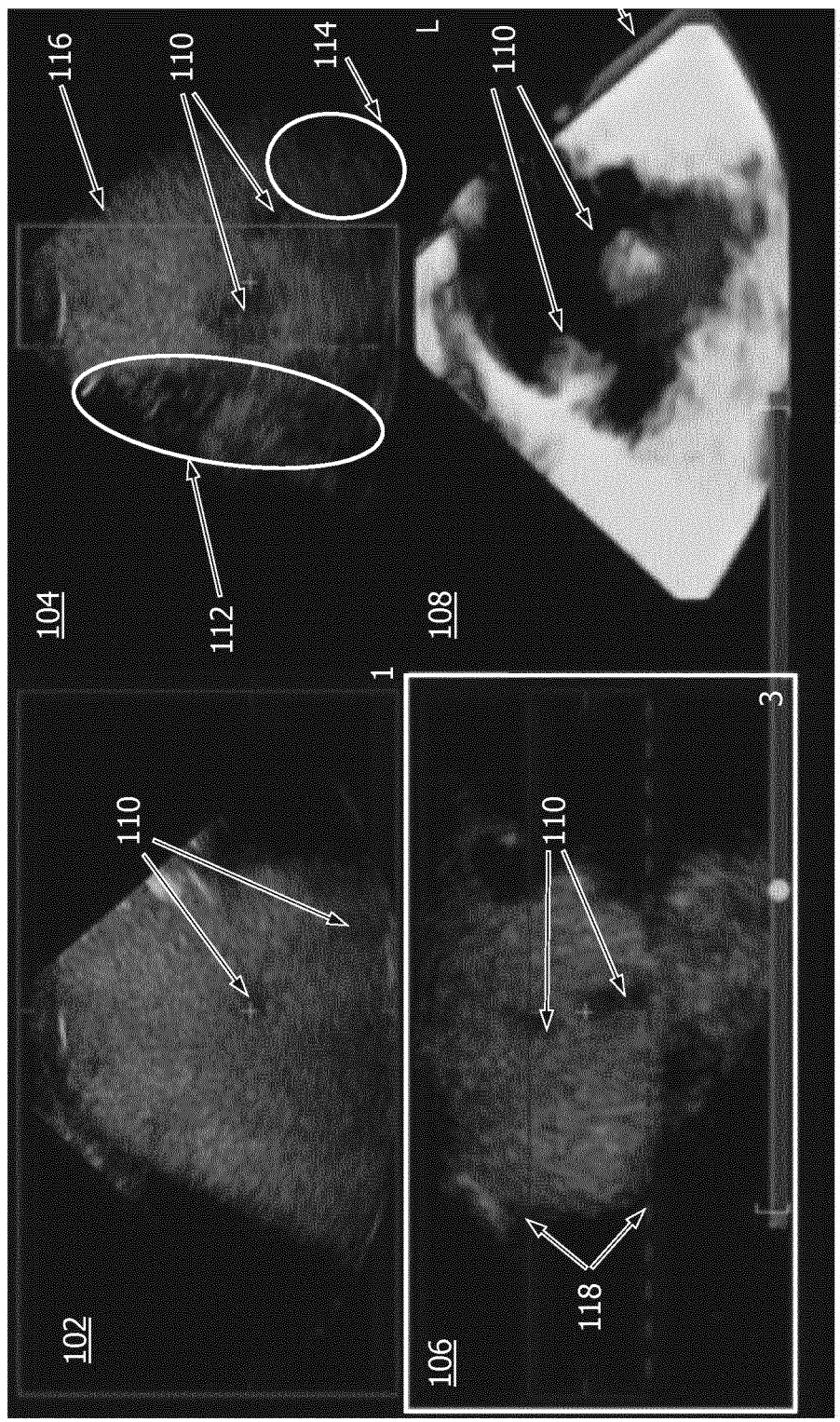
FIG. 1 shows representative ultrasound scans of a volume in a liver.

Inverted 3D renderings have the potential to highlight vessels and hypoechoic lesions within uniform/bright tissue, but the utility may be significantly limited by inversion of hypoechoic regions that do not contain features of interest (e.g., areas of no signal or noise), but are included in the 3D rendered image FIG. 1 shows representative ultrasound scans of a volume in a liver. An example of where an inverted render may be desirable is in gastrointestinal (GI) applications, for example, liver imaging. A common issue is that the liver may be imaged through ribs or other difficult acoustic windows. The liver may be contained centrally in the imaging volume, but the outer region of the volume contains noise. Shadowing from ribs, bone, and/or refraction may produce bright artifacts in inverted render. These regions that do not contain useful signals, but may dominate the final inverted render, which projects inward from the outside edges.

As shown in FIG. 1, pane 102 shows a coronal slice of the liver through the center of the scanned volume. Pane 104 shows a sagittal slice of the liver through the center of the scanned volume and pane 106 shows a transverse slice of the liver through the center of the scanned volume. Two hypoechoic lesions 110 can be observed in all three panes. Several regions of low signal can also be observed in the panes, for example, within regions 112 and 114 in pane 104. These low signal regions 112, 114 may be the result of rib shadowing, poor acoustic coupling of the transducer with the subject's skin, and/or other factors. Regardless of the cause of the low signal, the low signal regions 112, 114 on the periphery of the volume may appear as bright "walls" in an inverted render, partially or fully obscure the hypoechoic lesions 110. The bright walls may be "trimmed" away by manually selecting a limited region of interest (ROI) within the volume to render. As shown in panes 104 and 106, a user may interact with the ultrasound system via a user interface to define a ROI of the volume to render by manipulating the size and position of box 116 and/or lines 118.

Pane 108 shows an inverted render of the volume manually trimmed by the user. While the hypoechoic lesions 110 are visible in the inverted render, artifacts remain in the orthogonal dimensions, which may cause problems in rotating the inverted render. Further trimming may remove these artifacts, but it may reduce the ability to rotate the 3D data and keep the lesions 110 in the box 116.

Several rendering techniques for 3D datasets exist including surface rendering and maximum intensity rendering. Many rendering techniques project parallel rays through the 3D dataset from a viewpoint that is selected by a user or pre-set by the system to render a 2D representation (e.g., image) of the volume associated with the 3D dataset. In surface rendering, the "nearest" voxels are rendered to generate the 2D image. That is, the voxels "hit" by the parallel rays first are displayed. In maximum intensity rendering, the voxels with the highest intensity along the rays are rendered or the highest intensity within a given depth range. Both surface and maximum projection techniques may be used for inverted rendering.

Figure 2:
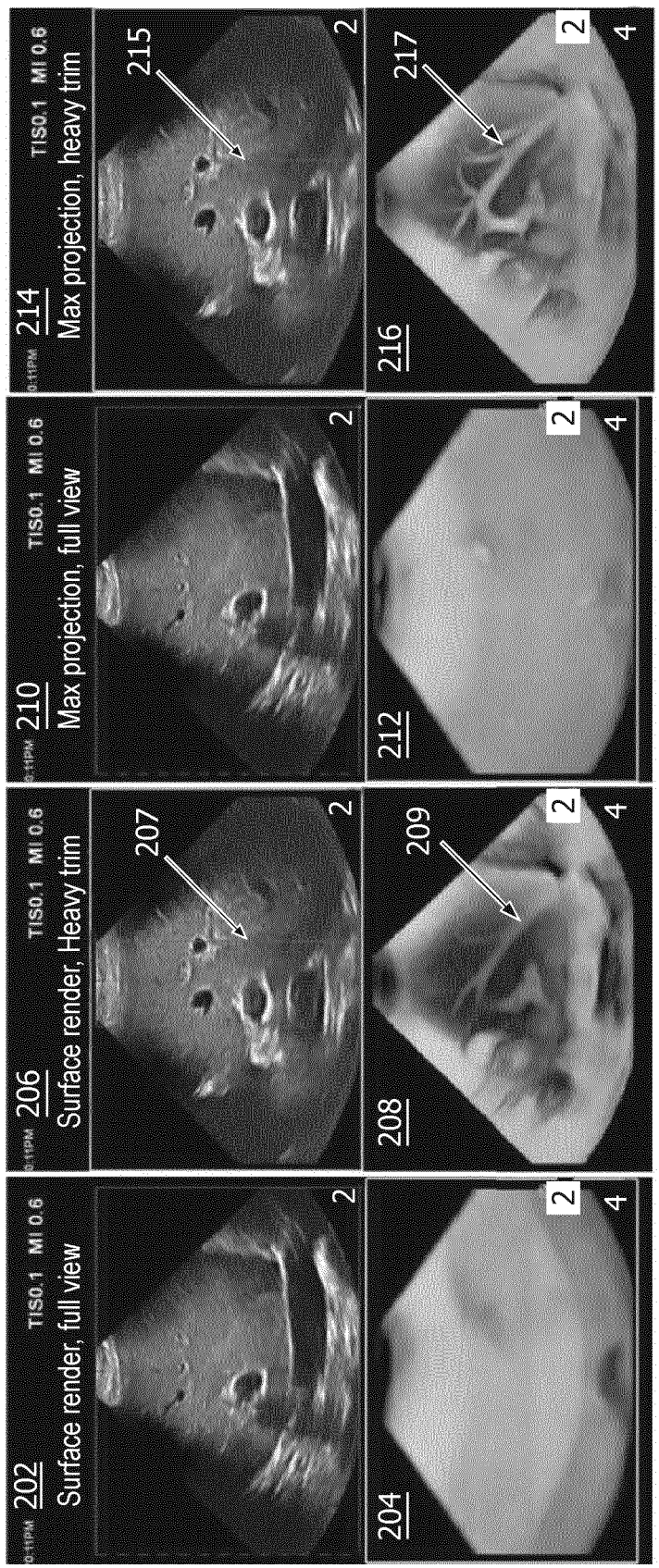
FIG. 2 shows representative ultrasound scans of a volume in a liver.

FIG. 2 shows representative ultrasound scans of a liver with blood vessels. Pane 202 shows a representative slice of the scanned volume and pane 204 shows an inverted render of the entire volume using a surface rendering technique. The low signal at the periphery of the volume almost completely obscures the blood vessels in the inverted render in pane 204. Pane 206 shows a representative slice of the scanned volume and a ROI box 207 set by a user. Pane 208 shows a surface render of the trimmed volume defined by ROI box 207. Blood vessels 209 are visible in the inverted render of the trimmed volume, however, some details remain obscured by inadequate trimming.

Pane 210 shows a representative slice of the scanned volume and pane 212 shows an inverted render of the entire volume using a maximum intensity technique. Similar to the surface render, the noise at the periphery of the volume nearly completely obscures any features of interest in the volume. Pane 214 shows a representative slice of the scanned volume and the ROI box 215 set by the user. Pane 216 shows a maximum intensity render of the trimmed volume defined by ROI box 215. Blood vessels 217 are visible in the inverted render of the trimmed volume. While maximum intensity rendering may provide somewhat more detail than surface rendering, as seen in FIG. 2, detail is still obscured by the noise at the periphery of the volume. Both the surface and maximum intensity renderings require not only manual trimming of the volume to be rendered, but also manual user adjustments to imaging parameters such as threshold values, opacity, and transparency.

As shown in FIGS. 1 and 2, there is a high user workflow burden to isolate features of interest, such as using narrow ROI boxes to eliminate cluttered areas, and adjusting settings such as threshold and transparency. In post-acquisition analysis when it is known a priori that hypoechoic features have been captured in the volume, this process is time-consuming, but may be acceptable. In live (4D) imaging for the purposes of diagnosis, the interfering artifacts and workflow burden may limit the utility of the inverted rendering technique's usefulness significantly.

Ideally, an inverted render in 3D or 4D should allow simple visualization of hypoechoic regions with minimized workflow burden. In this disclosure, a 'smart invert' approach that automates aspects of segmenting the 3D dataset in order to project only regions of the volume known to contain signal from a region of interest (e.g., tissue) rather than signal due to noise (also referred to simply as noise). Additional enhancements may optionally be included such as enhancing of certain classes of features (e.g. features that meet a criterion of 'vessel-ness' versus those that don't) or feature sizes (e.g. large vessels vs. small) in the final inverted render. Some or all of the additional enhancements may be controlled by a user.

As described herein, a system, such as an ultrasound imaging system, may receive or acquire a three dimensional (3D) dataset that defines a volume. For example, the 3D dataset may include data from echo signals acquired from scanning the volume with an ultrasound transducer. The 3D dataset may be stored on a non-transitory computer readable medium included with the system. The system may include a processor configured to sort the data points of the 3D dataset into one of two sets. Based on the sorting, the processor may generate a mask that corresponds to the 3D dataset. That is, the mask may have the same dimensions and number of data points as the 3D data set such that each data point in the mask corresponds to a data point in the 3D data set. Data points of the mask that correspond to data points of the 3D dataset that are sorted into a first set may be set to a first value (e.g., 1) and data points of the mask that correspond to data points of the 3D dataset that are sorted into a second set may be set to a second value (e.g., 0). In some examples, the data points may be sorted into more than two sets.

The data points may be sorted into the sets in a variety of ways. For example, the sorting of the data points into the two sets may be performed by comparing each data point to a threshold value. Data points above the threshold value may be sorted in the first set and data points below the threshold value may be sorted into the second set. Data points equal to the threshold value may be sorted into the first set in some examples or into the second set in other examples. The threshold value used to generate the mask may be pre-set in the system in some applications. In other applications, the threshold value may be based on a type of exam performed (e.g., liver exam, cardiac exam). For common exams, typical values associated with tissues and/or other structures of interest may be well known and may be used to set the threshold value. In some embodiments, the system may include a user interface that is configured to receive user inputs. A user may manually set the threshold value and/or indicate the type of exam to load a pre-set threshold value by providing an input via the user interface.

In another example, the sorting of the data points into the sets may be performed by a fuzzy logic operation. For example, the fuzzy logic operation may include a first threshold value and a second threshold value. The first threshold value may be higher than the second threshold value. Data points having values above the first threshold value may be assigned to a first set and data points having values below the second threshold value may be assigned to a second set. In some examples, data points in the first set may be rendered and data points in the second set may not be rendered. The data points having values between the two threshold values may be assigned to a third set in some examples. In some examples, data points in the third set may be further sorted into sub-sets (e.g., based on a sigmoid fuzzy membership function and/or other fuzzy membership function). Data points in the third set may contribute to the 3D render in some examples, but may be rendered differently than those in the first set. For example, data points in the third set may be rendered with a low opacity value (e.g., high translucency). In another example, data points in the third set may be rendered with reduced intensity values.

In another example, a trained deep learning algorithm may characterize individual data point based on one or more learned features (e.g., proximity to other data points of similar or dissimilar values, intensity gradient across data points). Based on the characterization, the individual data points may be sorted into two or more sets.

The mask may be applied to the 3D dataset to segment the 3D dataset into data to be used in an inverted render and data to be ignored or discarded during the inverted render. For example, the processor may determine an outer boundary of the data points of the mask set to the first value and define a second volume within the first volume based on the outer boundary. The second volume may define a subset of the 3D dataset that includes data points in the 3D dataset associated with signal from a region of interest. Data points outside the second volume may define the data points in the 3D dataset associated with noise. Based on the segmentation with the mask, the processor may generate an inverted render from the subset of the 3D dataset. The inverted render may be generated by any currently known or future technique, for example, surface rendering or maximum intensity rendering. The inverted render may be provided on a display to a user and/or stored in a memory of the system for later viewing and/or analysis.

In some embodiments, the processor may be configured to filter the 3D dataset prior to generating the mask. Filtering the 3D dataset may reduce the occurrence of misclassifying signals from the region of interest as noise and vice versa. For example, filtering may reduce the value of at least some of the data points associated with noise such that fewer data points associated with noise have a value above a threshold value. In another example, filtering may increase a difference between values of data points associated with the signal and values of data points associated with noise. This may reduce the number of data points associated with signal from the region of interest having a value below a threshold value and/or reduce the number of data points associated with noise having a value above a threshold value. In some embodiments, the results of the filtering may be used to set a threshold value. As will be described in more detail later, a variety of filtering techniques may be used including, but not limited to, smoothing kernels and adaptive smoothing (e.g., persistence) algorithms. The filtering technique used may be pre-set by the system or may be selected by the user.

Figure 3:
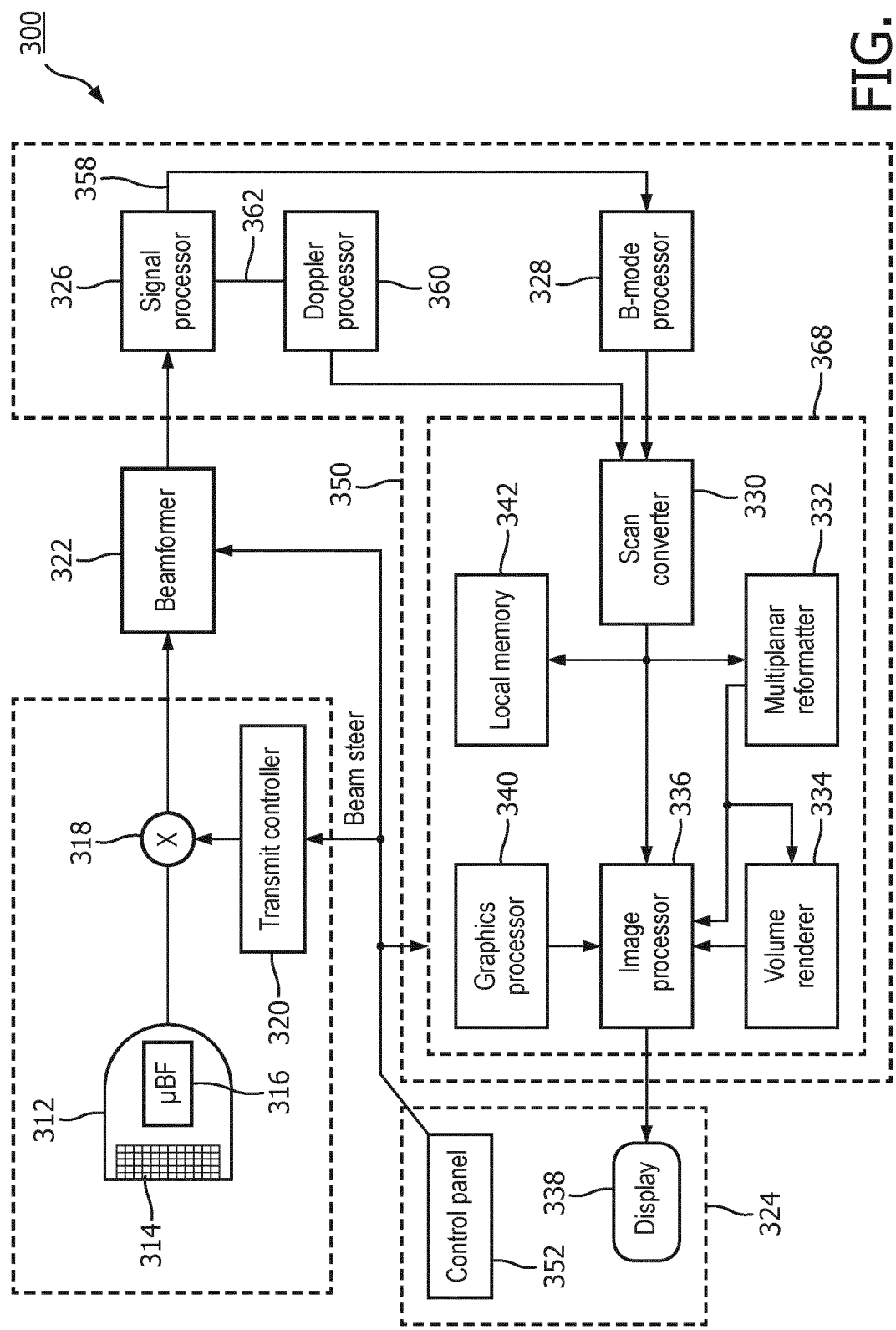
FIG. 3 is a block diagram of an ultrasound imaging system arranged in accordance with some embodiments of the present disclosure.

FIG. 3 shows a block diagram of an ultrasound imaging system 300 constructed in accordance with the principles of the present disclosure. An ultrasound imaging system 300 according to the present disclosure may include a transducer array 314, which may be included in an ultrasound probe 312, for example an external probe or an internal probe such as an intravascular ultrasound (IVUS) catheter probe. In other embodiments, the transducer array 314 may be in the form of a flexible array configured to be conformally applied to a surface of subject to be imaged (e.g., patient). The transducer array 314 is configured to transmit ultrasound signals (e.g., beams, waves) and receive echoes responsive to the ultrasound signals. A variety of transducer arrays may be used, e.g., linear arrays, curved arrays, or phased arrays. The transducer array 314, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction.

In some embodiments, the transducer array 314 may be coupled to a microbeamformer 316, which may be located in the ultrasound probe 312, and which may control the transmission and reception of signals by the transducer elements in the array 314. In some embodiments, the microbeamformer 316 may control the transmission and reception of signals by active elements in the array 314 (e.g., an active subset of elements of the array that define the active aperture at any given time).

In some embodiments, the microbeamformer 316 may be coupled, e.g., by a probe cable or wirelessly, to a transmit/receive (T/R) switch 318, which switches between transmission and reception and protects the main beamformer 422 from high energy transmit signals. In some embodiments, for example in portable ultrasound systems, the T/R switch 318 and other elements in the system can be included in the ultrasound probe 312 rather than in the ultrasound system base, which may house the image processing electronics. An ultrasound system base typically includes software and hardware components including circuitry for signal processing and image data generation as well as executable instructions for providing a user interface.

The transmission of ultrasonic signals from the transducer array 314 under control of the microbeamformer 316 is directed by the transmit controller 320, which may be coupled to the T/R switch 318 and a main beamformer 322. The transmit controller 320 may control the direction in which beams are steered. Beams may be steered straight ahead from (orthogonal to) the transducer array 314, or at different angles for a wider field of view. The transmit controller 420 may also be coupled to a user interface 324 and receive input from the user's operation of a user control. The user interface 324 may include one or more input devices such as a control panel 352, which may include one or more mechanical controls (e.g., buttons, encoders, etc.), touch sensitive controls (e.g., a trackpad, a touchscreen, or the like), and/or other known input devices.

In some embodiments, the partially beamformed signals produced by the microbeamformer 316 may be coupled to a main beamformer 322 where partially beamformed signals from individual patches of transducer elements may be combined into a fully beamformed signal. In some embodiments, microbeamformer 316 is omitted, and the transducer array 314 is under the control of the beamformer 322 and beamformer 322 performs all beamforming of signals. In embodiments with and without the microbeamformer 316, the beamformed signals of beamformer 322 are coupled to processing circuitry 350, which may include one or more processors (e.g., a signal processor 326, a B-mode processor 328, a Doppler processor 360, and one or more image generation and processing components 368) configured to produce an ultrasound image from the beamformed signals (i.e., beamformed RF data).

The signal processor 326 may be configured to process the received beamformed RF data in various ways, such as bandpass filtering, decimation, I and Q component separation, and harmonic signal separation. The signal processor 326 may also perform additional signal enhancement such as speckle reduction, signal compounding, and noise elimination. The processed signals (also referred to as I and Q components or IQ signals) may be coupled to additional downstream signal processing circuits for image generation. The IQ signals may be coupled to a plurality of signal paths within the system, each of which may be associated with a specific arrangement of signal processing components suitable for generating different types of image data (e.g., B-mode image data, Doppler image data). For example, the system may include a B-mode signal path 358 which couples the signals from the signal processor 326 to a B-mode processor 328 for producing B-mode image data.

The B-mode processor can employ amplitude detection for the imaging of structures in the body. The signals produced by the B-mode processor 328 may be coupled to a scan converter 330 and/or a multiplanar reformatter 332. The scan converter 330 may be configured to arrange the echo signals from the spatial relationship in which they were received to a desired image format. For instance, the scan converter 330 may arrange the echo signal into a two dimensional (2D) sector-shaped format, or a pyramidal or otherwise shaped three dimensional (3D) format. The multiplanar reformatter 332 can convert echoes which are received from points in a common plane in a volumetric region of the body into an ultrasonic image (e.g., a B-mode image) of that plane, for example as described in U.S. Pat. No. 6,443,896 (Detmer). The scan converter 330 and multiplanar reformatter 332 may be implemented as one or more processors in some embodiments.

A volume renderer 334 may generate an image (also referred to as a projection, render, or rendering) of the 3D dataset as viewed from a given reference point, e.g., as described in U.S. Pat. No. 6,530,885 (Entrekin et al.). The volume renderer 334 may be implemented as one or more processors in some embodiments. The volume renderer 334 may generate a render, such as a positive render or a negative render, by any known or future known technique such as surface rendering and maximum intensity rendering.

According to the principles of the present disclosure, the volume renderer 334 may segment the 3D dataset prior to generating an inverted render. The segmenting may be performed by applying a mask to the 3D dataset. The mask may be generated by the volume renderer 334 by sorting the data points in the 3D dataset into two sets (e.g., data points to be rendered and data points to be omitted from the render). In some examples, the volume renderer 334 may set data points in the mask corresponding to data points in the 3D dataset having values above a threshold value to a first value (e.g., 1) corresponding to a first set that includes data to be rendered and data points in the mask corresponding to data points in the 3D dataset having values below a threshold value to a second value (e.g., 0) corresponding to a second set that includes data not to be rendered. The outer boundary of the data points in the mask corresponding to the first value may define a subset of the 3D dataset. The volume renderer 334 may then generate an inverted render of only the subset of the 3D dataset (e.g., the masked 3D dataset). The data points of the 3D volume outside the outer boundary may be ignored or discarded by the volume renderer 334.

The subset of the 3D dataset may include data points within the outer boundary that are set to the second value in the mask. These data points may correspond to hypoechoic regions of interest in some applications. However, because volume renderer 334 uses the outer boundary of the data points equal to the first value in the mask, the hypoechoic regions within the subset are not ignored or discarded by the volume renderer 334 when generating the inverted render.

In some applications, hypoechoic regions of interest may extend from within the region defined by the outer boundary to beyond the outer boundary. For example, a blood vessel may pass through the entire scanned volume defined by the 3D dataset. In this example, portions of the blood vessel that fall outside the outer boundary defined by the mask may be ignored or discarded by the volume renderer 334 when generating an inverted render. Optionally, to preserve features of hypoechoic regions that extend beyond the subset of the 3D dataset, morphological operations and/or feature detection may be applied to the mask. These operations may adjust the outer boundary of the data points set to the first value. Morphological and/or feature detection may use known or future known image segmentation techniques such as 'open,' 'fill,' and 'walk-out' algorithms. Artificial intelligence or deep learning algorithms trained to recognize morphological features may also be used to adjust the mask.

As mentioned previously, in some examples, a threshold value may be used to sort the data points into two sets. The threshold value used to generate the mask may be set in a variety of ways. A difficulty in any segmentation problem is that there may be data points associated with signal from the ROI that are below the threshold value and data points associated with noise that are above the threshold value. The threshold value should be set as accurately as possible. If the threshold value is set aggressively low, the inverted render may not include portions of the tissue. However, if the threshold value is set too high, hypoechoic regions of interest may be obscured. In some applications, the volume renderer 334 may pre-process the 3D dataset prior to generation of the mask to reduce the number of signal data points having values below the threshold and the number of noise data points having values above the threshold value. As will be described in more detail further below, a variety of filtering techniques may be used.

In some embodiments, the system may include a Doppler signal path 362 which couples the output from the signal processor 326 to a Doppler processor 360. The Doppler processor 160 may be configured to estimate the Doppler shift and generate Doppler image data. The Doppler image data may include color data which is then overlaid with B-mode (i.e. grayscale) image data for display. The Doppler processor 360 may be configured to filter out unwanted signals (i.e., noise or clutter associated with non-moving tissue), for example using a wall filter. The Doppler processor 360 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo further threshold detection to further reduce noise, as well as segmentation and post-processing such as filling and smoothing. The velocity and power estimates may then be mapped to a desired range of display colors in accordance with a color map. The color data, also referred to as Doppler image data, may then be coupled to the scan converter 330, where the Doppler image data may be converted to the desired image format and overlaid on the B-mode image of the tissue structure to form a color Doppler or a power Doppler image. For example, Doppler image data may be overlaid on an inverted render of the tissue structure. This may allow visualization of fluid flow within hypoechoic regions (e.g., blood vessels).

Output (e.g., B-mode images, Doppler images) from the scan converter 330, the multiplanar reformatter 332, and/or the volume renderer 334 may be coupled to an image processor 336 for further enhancement, buffering and temporary storage before being displayed on an image display 338.

According to principles of the present disclosure, the image processor 336 may perform some or all of the pre and/or post-processing of the 3D dataset prior to the volume renderer 334 generating the inverted render. For example, in some embodiments, the image processor 336 may filter the 3D dataset and/or perform feature recognition on the mask. The image processor 336 may provide the filtered 3D dataset and/or modified mask to the volume renderer 334 for generating the inverted render. In some embodiments, the image processor 336 may perform post-processing of the inverted render, for example, adjustment of opacity/transparency settings, smoothing, contrast enhancement, and/or depth color encoding.

A graphics processor 340 may generate graphic overlays for display with the images. These graphic overlays can contain, e.g., standard identifying information such as patient name, date and time of the image, imaging parameters, and the like. For these purposes the graphics processor may be configured to receive input from the user interface 324, such as a typed patient name or other annotations. The user interface 344 can also be coupled to the multiplanar reformatter 332 for selection and control of a display of multiple multiplanar reformatted (MPR) images.

The system 300 may include local memory 342. Local memory 342 may be implemented as any suitable non-transitory computer readable medium (e.g., flash drive, disk drive). Local memory 342 may store data generated by the system 300 including B-mode images, masks, executable instructions, inputs provided by a user via the user interface 324, or any other information necessary for the operation of the system 300.

As mentioned previously system 300 includes user interface 324. User interface 324 may include display 338 and control panel 352. The display 338 may include a display device implemented using a variety of known display technologies, such as LCD, LED, OLED, or plasma display technology. In some embodiments, display 338 may comprise multiple displays. The control panel 352 may be configured to receive user inputs (e.g., threshold value, filter type, render type). The control panel 352 may include one or more hard controls (e.g., buttons, knobs, dials, encoders, mouse, trackball or others). In some embodiments, the control panel 352 may additionally or alternatively include soft controls (e.g., GUI control elements or simply, GUI controls) provided on a touch sensitive display. In some embodiments, display 338 may be a touch sensitive display that includes one or more soft controls of the control panel 352.

In some embodiments, various components shown in FIG. 3 may be combined. For instance, image processor 336 and graphics processor 340 may be implemented as a single processor. In another example, the scan converter 330 and multiplanar reformatter 332 may be implemented as a single processor. In some embodiments, various components shown in FIG. 3 may be implemented as separate components. For example, signal processor 326 may be implemented as separate signal processors for each imaging mode (e.g., B-mode, Doppler). In some embodiments, one or more of the various processors shown in FIG. 3 may be implemented by general purpose processors and/or microprocessors configured to perform the specified tasks. In some embodiments, one or more of the various processors may be implemented as application specific circuits. In some embodiments, one or more of the various processors (e.g., image processor 336) may be implemented with one or more graphical processing units (GPU).

Figure 8:
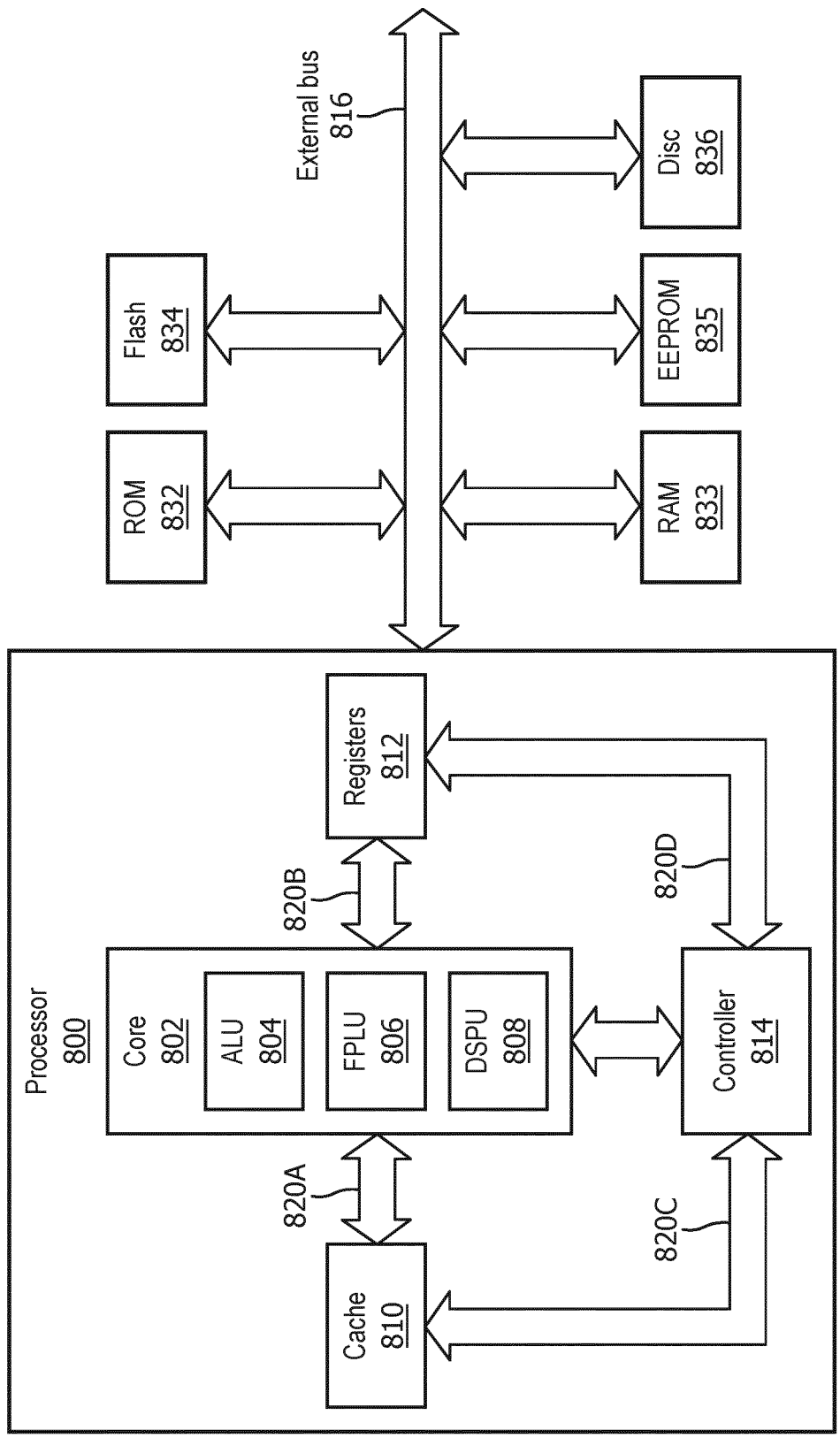
FIG. 8 is a block diagram illustrating an example processor in accordance with some embodiments of the present disclosure.

FIG. 8 is a block diagram illustrating an example processor 800 according to principles of the present disclosure. Processor 800 may be used to implement one or more processors described herein, for example, image processor 336 shown in FIG. 3. Processor 800 may be any suitable processor type including, but not limited to, a microprocessor, a microcontroller, a digital signal processor (DSP), a field programmable array (FPGA) where the FPGA has been programmed to form a processor, a graphical processing unit (GPU), an application specific circuit (ASIC) where the ASIC has been designed to form a processor, or a combination thereof.

The processor 800 may include one or more cores 802. The core 802 may include one or more arithmetic logic units (ALU) 804. In some embodiments, the core 802 may include a floating point logic unit (FPLU) 806 and/or a digital signal processing unit (DSPU) 808 in addition to or instead of the ALU 804.

The processor 800 may include one or more registers 812 communicatively coupled to the core 802. The registers 812 may be implemented using dedicated logic gate circuits (e.g., flip-flops) and/or any memory technology. In some embodiments the registers 812 may be implemented using static memory. The register may provide data, instructions and addresses to the core 802.

In some embodiments, processor 800 may include one or more levels of cache memory 810 communicatively coupled to the core 802. The cache memory 810 may provide computer-readable instructions to the core 802 for execution. The cache memory 810 may provide data for processing by the core 802. In some embodiments, the computer-readable instructions may have been provided to the cache memory 810 by a local memory, for example, local memory attached to the external bus 816. The cache memory 810 may be implemented with any suitable cache memory type, for example, metal-oxide semiconductor (MOS) memory such as static random access memory (SRAM), dynamic random access memory (DRAM), and/or any other suitable memory technology.

The processor 800 may include a controller 814, which may control input to the processor 800 from other processors and/or components included in a system (e.g., control panel 352 and scan converter 330 shown in FIG. 3) and/or outputs from the processor 800 to other processors and/or components included in the system (e.g., display 338 and volume renderer 334 shown in FIG. 3). Controller 814 may control the data paths in the ALU 804, FPLU 806 and/or DSPU 808. Controller 814 may be implemented as one or more state machines, data paths and/or dedicated control logic. The gates of controller 814 may be implemented as standalone gates, FPGA, ASIC or any other suitable technology.

The registers 812 and the cache 810 may communicate with controller 814 and core 802 via internal connections 820A, 820B, 820C and 820D. Internal connections may implemented as a bus, multiplexor, crossbar switch, and/or any other suitable connection technology.

Inputs and outputs for the processor 800 may be provided via a bus 816, which may include one or more conductive lines. The bus 816 may be communicatively coupled to one or more components of processor 800, for example the controller 814, cache 810, and/or register 812. The bus 816 may be coupled to one or more components of the system, such as display 338 and control panel 352 mentioned previously.

The bus 816 may be coupled to one or more external memories. The external memories may include Read Only Memory (ROM) 832. ROM 832 may be a masked ROM, Electronically Programmable Read Only Memory (EPROM) or any other suitable technology. The external memory may include Random Access Memory (RAM) 833. RAM 833 may be a static RANI, battery backed up static RAM, Dynamic RAM (DRAM) or any other suitable technology. The external memory may include Electrically Erasable Programmable Read Only Memory (EEPROM) 835. The external memory may include Flash memory 834. The external memory may include a magnetic storage device such as disc 836. In some embodiments, the external memories may be included in a system, such as ultrasound imaging system 300 shown in FIG. 3, for example local memory 342.

As mentioned above, filtering of the 3D dataset may be performed prior to generating the mask for segmenting. In some applications, filtering the 3D dataset may improve the accuracy of the segmentation (e.g., sorting). Filtering may be performed by a variety of known techniques, for example, smoothing with a kernel that averages neighboring voxels, adaptive thresholding, and histogram equalization and remapping. Filtering the 3D dataset may create a uniform background signal and create more separation between the noise (e.g., background) and tissue signal, which may allow for more accurate segmentation between noise and signal-containing regions.

Another filtering technique that may be used is an adaptive smoothing algorithm, such as a persistence algorithm (PA). The PA may negatively bias the intensity of voxels likely to be noise based on measurements or estimations of the true noise floor, and subsequently smooth the value relative to neighboring voxels. With the PA, voxels classified as 'true signal' retain original intensity and remain unblurred, preserving edges while blackening hypoechoic regions. The PA may compare data points in the 3D dataset (e.g., voxels) to a noise model and determine its likelihood of containing signal or noise. Data points found to have a low likelihood of having noise are left unchanged while data points found to have a high likelihood of having noise are reduced in value. The probability value defining a data point having a high or low likelihood of having noise may be pre-set in a system or set by a user. Similarly, the amount of reduction of the values of data points likely to include noise may be pre-set in a system or set by a user. The noise model may be generated in a variety of ways. For example, the noise model may be based on the known noise power versus gain of receive amplifiers of an imaging system. In another example, the noise model may be based on cross correlating consecutively received volumes from a stationary imaging object such as a phantom or air. Other ways of generating the noise model may also be used. A more detailed description of the PA may be found in U.S. Application No. 62/621,187, which is incorporated herein by reference for any purpose.

In some applications, an output of the filtering may be used to set one or more threshold values for sorting the data points to generate the mask. For example, estimations of the noise floor in the PA may be used to set a threshold value above the noise floor. In another example, the data from the histogram equalization may be used to select a threshold between a histogram peak associated with noise and a histogram peak associated with signal. In some examples, such as fuzzy logic examples, a first threshold value may be selected based on the histogram peak associated with noise and a second threshold value may be selected based on the histogram peak associated with signal. In some applications, the processed images and/or data from the filtering may be provided to a user to assist the user in selecting one or more threshold values for sorting data points to generate the mask.

Figure 4:
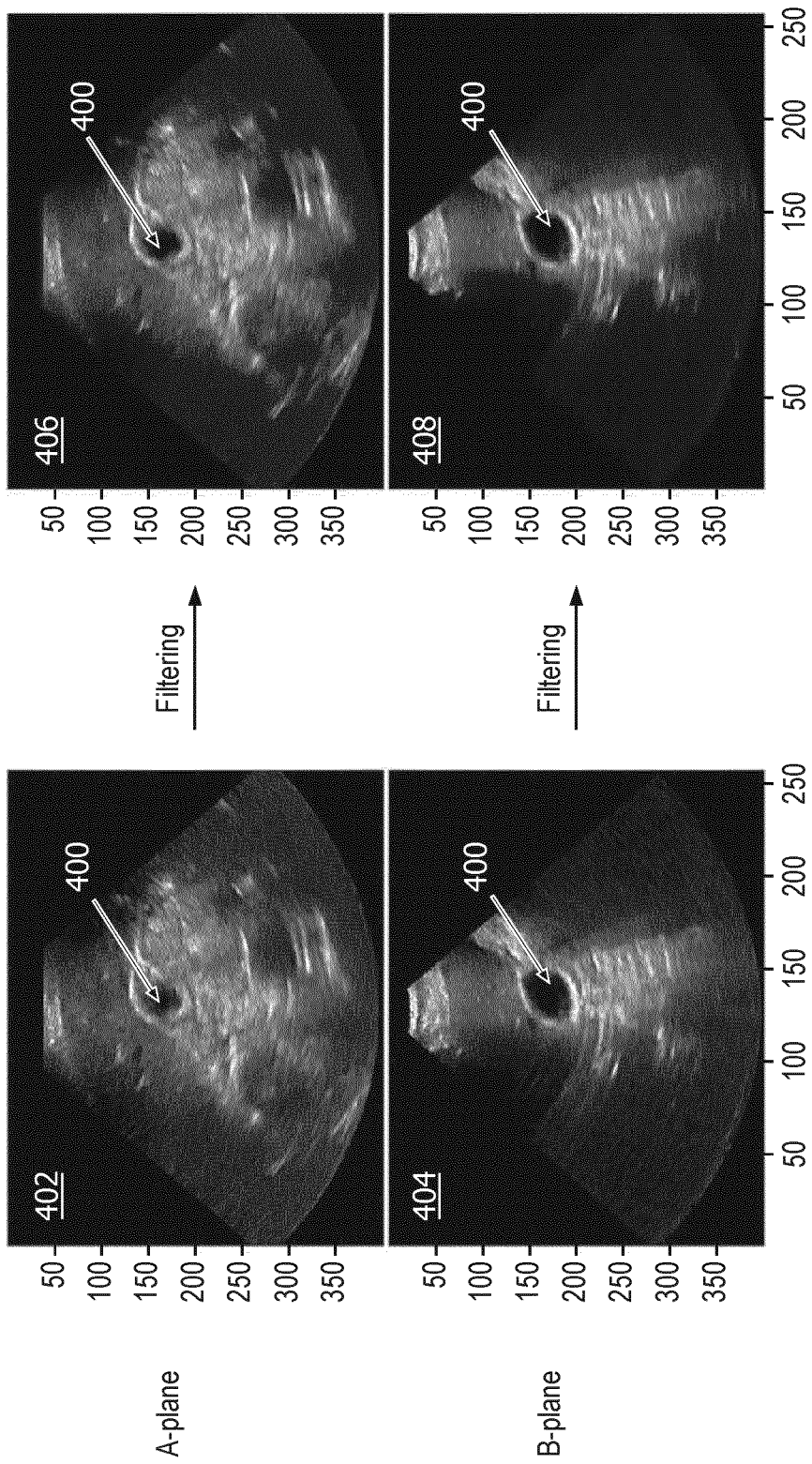
FIG. 4 shows representative ultrasound scans of a volume including a gall bladder and the scans processed in accordance with some embodiments of the present disclosure.

FIG. 4 shows representative ultrasound scans of a volume including a gall bladder 400 and the scans processed (e.g., filtered) in accordance with some embodiments of the present disclosure. Panes 402 shows the A-plane of the volume and pane 404 shows the B-plane of the volume. The periphery of the image in both panes 402 and 404 have pixels that are associated with noise, but the values of some of those pixels are similar in value to the pixels that are associated with the tissue surrounding the gall bladder 400. Accordingly, generating a mask for a volume including panes 402 and 404 may mistakenly segment these areas of noise as tissue. Prior to generating the mask, panes 402 and 404 may be filtered. In the example shown in FIG. 4, a PA is used. Pane 406 shows the filtered A-plane and pane 408 shows the filtered B-plane. As can be seen in panes 406 and 408, the intensity (e.g., values) of the pixels associated with noise have been reduced. Sorting of data points to generate the mask may then be performed on the filtered 3D dataset. In some examples, the sorting may be based on a pre-set, user-driven, or algorithm-based threshold value(s). In other examples, the sorting may be based on deep learning or other sorting techniques. Optionally, morphological operations may be used to remove additional noise, disconnected regions, and/or fill holes inside the 'true signal' region that may be hypoechoic regions of interest such as lesions and vessels. Applying the mask to a volume including the processed panes 406 and 408 may more accurately segment the tissue and noise regions of the volume.

Figure 5:
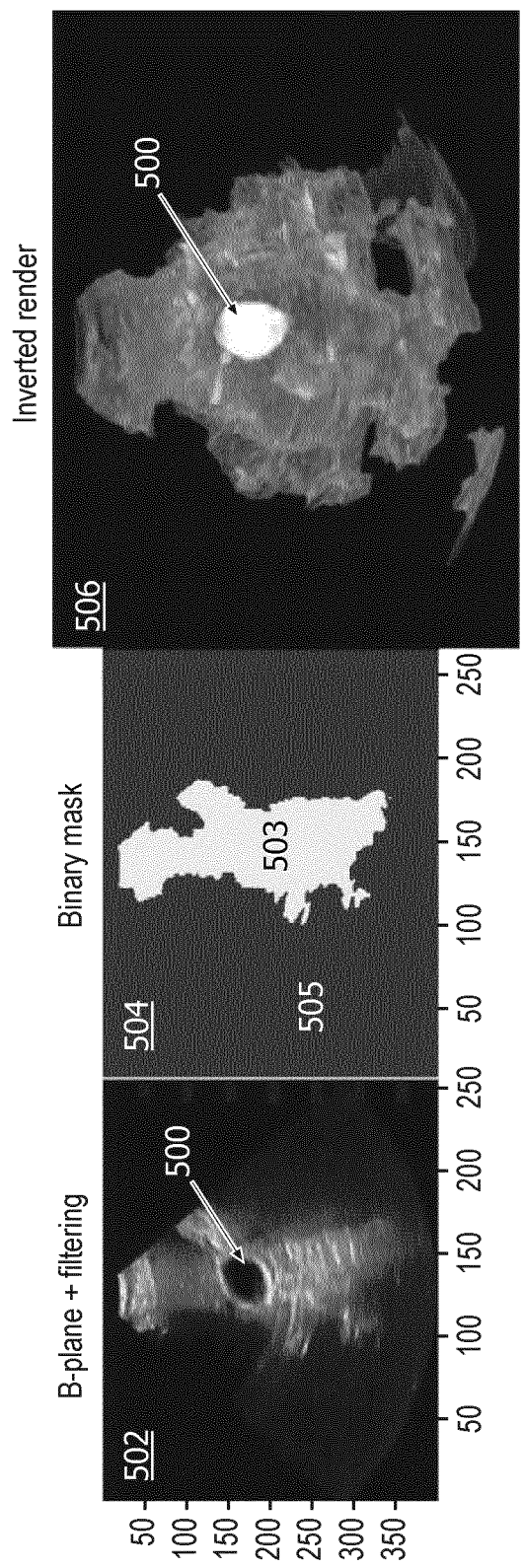
FIG. 5 shows a representative processed ultrasound scan, a mask, and an inverted render of the processed ultrasound scan in accordance with some embodiments of the present disclosure.

FIG. 5 shows a representative processed ultrasound scan of a volume including a gall bladder 500, a mask, and an inverted render of the processed ultrasound scan in accordance with some embodiments of the present disclosure. Pane 502 shows the processed B-plane from pane 408 in FIG. 4. As mentioned previously, the B-plane was processed by applying a PA filter. Pane 504 shows the mask generated for the B-plane shown in pane 502. While only the mask generated for the B-plane is shown, it is understood that the mask is generated for all planes in the volume (e.g., the entire 3D data set defining the scanned volume including the B-plane shown in pane 502).

The mask includes a first region 503 and a second region 505. The first region 503 includes data points of the mask set to a first value. The first region 503 corresponds to data points in the 3D dataset that include signal associated with tissue. The second region 505 includes data points of the mask set to a second value. The second region 505 corresponds to data points in the 3D dataset that include noise. The mask may be applied to the 3D dataset to determine which data points in the 3D dataset will be used in generating an inverted render. Only the subset of data of the 3D dataset associated with the first region 503 will be included in the inverted render.

Pane 506 shows an inverted render of the masked 3D dataset (e.g., the subset of the 3D dataset associated with the first region 503 of the mask). In the example shown in FIG. 5, the inverted render is generated using a maximum intensity rendering technique. The gall bladder 500 is visible in pane 506 and is not obscured by the bright noise 'walls' on the periphery of the scanned volume.

Optionally, prior to generating and/or displaying the inverted render, the masked 3D dataset may undergo further processing. For example, aspects such as opacity/transparency mapping, smoothing (e.g., based on feature size), contrast (e.g., based on histograms), and/or color-encoding may be adjusted. These adjustments may be adaptive based on the data and/or presets of an imaging system (e.g., expected values associated with types of exams). In this same stage, further enhancements may be made to adjust relative intensity/contrast of features determined to meet pre-set, user-driven, and/or algorithmic criteria, for example, vessel-ness, lack of vessel-ness, and/or feature size.

The resulting segmented and post-processed 3D dataset may be rendered using traditional techniques (e.g. surface render, maximum intensity render), and may produce a more artifact-independent and/or angle-independent render of hypoechoic features within the volume. If desired, current user controls over rendering can be preserved to allow the user the ability to alter aspects of the segmentation prior to generating the render and/or post-processing after rendering. For example, to customize the inverted render, the user may adjust which features (e.g., blood vessel near edge of volume) and/or regions are included and/or excluded from the inverted render. In some examples, the user may customize the render by setting a threshold value and/or by selecting regions of the volume with a selection box via the user interface. In another example, post-processing, a user may emphasize features through additional user interface controls (e.g., contrast, opacity).

Figure 6:
FIG. 6 shows a representative inverted render of a representative ultrasound scan without segmenting and an inverted render of the representative ultrasound scan with segmenting in accordance with some embodiments of the present disclosure.
Figure 6:
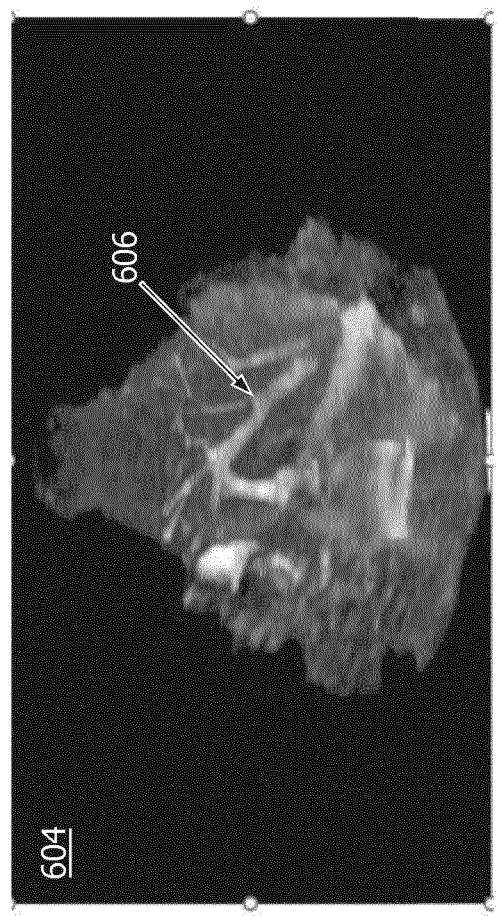

FIG. 6 shows a representative inverted render of a representative ultrasound scan without segmenting and an inverted render of the representative ultrasound scan with segmenting in accordance with some embodiments of the present disclosure. Pane 602 shows the inverted render of a volume of liver tissue including blood vessels 606 that was shown in pane 212 of FIG. 2. Pane 604 shows an inverted render of the volume of liver tissue including blood vessels 606 after the volume was segmented by a mask in accordance with principles of the present disclosure. The inverted render shown in pane 604 illustrates comparable results to the heavily manually cropped inverted render shown in pane 216 of FIG. 2. Accordingly, the preprocessing of 3D datasets according to the principles of the present disclosure may provide better visualization of hypoechoic regions of interest in inverted renders with reduced workflow burden.

Figure 7:
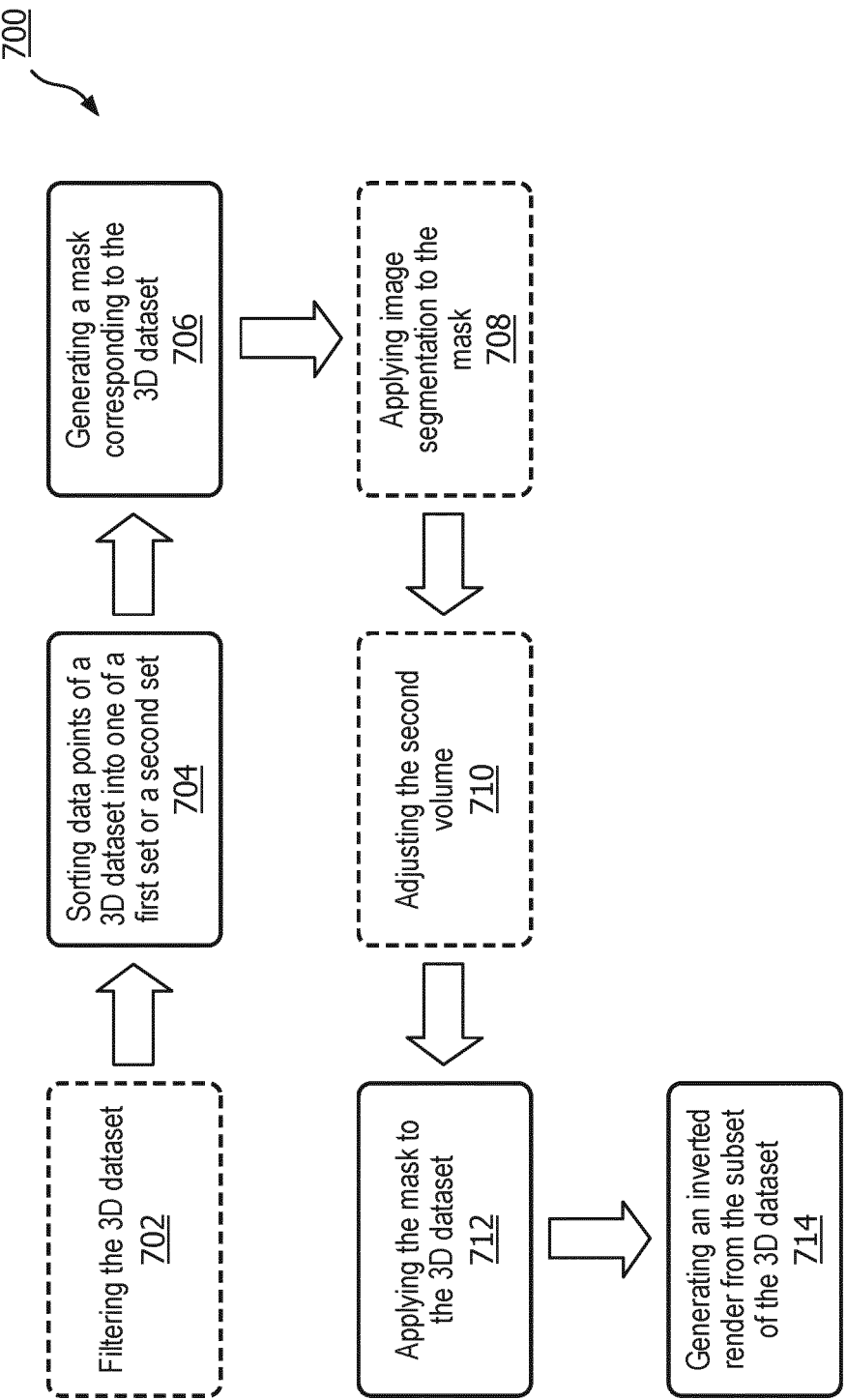
FIG. 7 is a flow chart of a method in accordance with some embodiments of the present disclosure.

FIG. 7 is a flow chart 700 of a method in accordance with some embodiments of the present disclosure. The method shown in FIG. 7 may be used to generate inverted renders according to principles of the present disclosure, for example the inverted renders shown in pane 506 of FIG. 5 and pane 604 of FIG. 6. In some applications, the method may be performed by a system, for example, an imaging system, such as system 300 shown in FIG. 3.

At block 704, a step of "sorting data points of a three 3D dataset into one of a first set or a second set" may be performed. The 3D dataset may define a first volume. In some examples, the data points of the 3D data set above a threshold value are sorted into the first set and data points of the 3D data set below the threshold value are sorted into the second set. In some examples, the threshold value is based on a tissue type being scanned. In some examples, the threshold value is set by a user. In some examples, the data points may be sorted into more than two sets.

Optionally, "filtering the 3D dataset" may be performed at block 702 prior to comparing data points of the 3D data set to the threshold value. This may increase a difference between signal values and noise values. The filtering may include applying two-dimensional or three-dimensional smoothing kernel, a histogram equalization and remapping algorithm, and/or applying an adaptive smoothing (e.g., persistence) algorithm. In some examples, the threshold value is set based on the filtering.

At block 706, "generating a mask corresponding to the 3D dataset" may be performed. Data points of the mask corresponding to data points of the 3D dataset sorted into the first set may be set to a first value and data points of the mask corresponding to data points of the 3D dataset sorted into the second set may be set to a second value. In some examples, where the data points are sorted into more than two sets, data points of the mask may be set to other values corresponding to the additional sets. An outer boundary of the data points of the mask set to the first value may define a second volume within the first volume. In some examples, an outer boundary of data points of the mask set to the first value and/or other values may be determined to define the second volume. Optionally, blocks 708 and 710 may be performed. At block 708, "applying image segmentation to the mask" may be performed. The image segmentation may recognize morphological features that extend from the second volume to the first volume. At block 710, a step of "adjusting the second volume" may be performed. This may adjust the second volume to include the morphological features recognized at block 708.

At block 712, "applying the mask to the 3D dataset" may be performed. The mask may be applied such that data points of the 3D dataset corresponding to data points outside the second volume are discarded to generate a subset of the 3D dataset. At block 714, "generating an inverted render from the subset of the 3D dataset" may be performed. In some examples, certain data points in the 3D data set in the second volume may be rendered differently than other data points. For example, data points having values between two threshold values may be rendered with a lower opacity than data points having values above a higher of the two threshold values (e.g., in a fuzzy logic operation).

In some embodiments, the steps associated with some or all of the blocks may be performed by a volume renderer, for example, volume renderer 334 of system 300 in FIG. 3. In some embodiments, some of the steps may be performed by an image processor, for example, image processor 336 in FIG. 3. For example, blocks 702, 704, 706, 708, 710, and/or 712 may be performed by an image processor and block 714 may be performed by a volume renderer. In another example, blocks 704-714 are performed by a volume renderer and block 702 is performed by the image processor. Other divisions of the blocks between the volume renderer and image processor may also be used.

The systems and methods described herein for preprocessing the 3D data prior to generating an inverted render may reduce the obscuring of hypoechoic regions of interest by noise in some applications. The systems and methods described herein may reduce workflow burden for users by automating at least some of the segmentation steps in some applications.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software, and/or firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instructions to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present systems and methods and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present systems and methods as set forth in the claims that follow. Accordingly, the specification and drawings are to be regarded in an illustrative manner and are not intended to limit the scope of the appended claims.

What is claimed is:

1. A method comprising:
   sorting data points of a three dimensional (3D) dataset acquired by an ultrasound imaging system into one of a first set or a second set, wherein the 3D dataset defines a first volume;
   generating a mask corresponding to the 3D dataset, wherein data points of the mask corresponding to data points of the 3D dataset sorted into the first set are set to a first value and data points of the mask corresponding to data points of the 3D dataset sorted into the second set are set to a second value, wherein an outer boundary of the data points of the mask set to the first value defines a second volume within the first volume;
   applying the mask to the 3D dataset such that data points of the 3D dataset corresponding to data points outside the second volume are discarded to generate a subset of the 3D dataset; and
   generating an inverted render from the subset of the 3D dataset, wherein generating the inverted render comprises rendering data points representing higher intensity signals with darker pixels than pixels used to render data points representing lower intensity signals,
   further comprising filtering the 3D dataset to increase a difference between signal values and noise values prior to sorting the data points of the 3D dataset.

2. The method of claim 1, wherein the data points of the 3D data set above a threshold value are sorted into the first set and data points of the 3D data set below the threshold value are sorted into the second set.

3. The method of claim 1, wherein the data points of the 3D data set are further sorted into a third set, wherein data points of the mask corresponding to data points of the 3D dataset sorted into the third set are set to a third value.

4. The method of claim 3, wherein the data points of the 3D data set sorted into the third set are rendered differently in the inverted render compared to the data points of the 3D data set sorted into the first set or the second set.

5. The method of claim 4, wherein the data points of the 3D data set sorted into the third set are rendered with a lower opacity value than the data points of the 3D data set sorted into the first set.

6. The method of claim 1, wherein a threshold value is set based on the filtering.

7. The method of claim 1, wherein filtering the 3D dataset comprises applying a two-dimensional or three-dimensional smoothing kernel; or applying a histogram equalization and remapping algorithm, or applying an adaptive smoothing algorithm.

8. The method of claim 2, wherein the threshold value is based on a tissue type being scanned.

9. The method of claim 1, further comprising:
   applying image segmentation to the mask to recognize morphological features that extend from the second volume to the first volume; and
   adjusting the second volume to include the morphological features.

10. The method of claim 1, wherein the sorting the data points is performed by fuzzy logic.

11. The method of claim 1, wherein sorting the data points is performed by a deep learning algorithm.

12. A system comprising:
   a non-transitory computer readable medium including a three dimensional (3D) dataset acquired by an ultrasound imaging system, the dataset defining a volume; and
   a processor configured to:
      sort data points of the 3D dataset into one of a first set or a second set;
      generate a mask corresponding to the 3D dataset, wherein data points of the mask corresponding to data points of the 3D dataset sorted into the first set are set to a first value and data points of the mask corresponding to data points of the 3D dataset sorted into the second set are set to a second value;
      determine an outer boundary of the data points of the mask set to the first value;
      define a second volume within the first volume based on the outer boundary;
      apply the mask to the 3D dataset to discard data points of the 3D dataset corresponding to data points outside the second volume to generate a subset of the 3D dataset; and
      generate an inverted render from the subset of the 3D dataset, wherein the inverted render is generated by rendering data points representing higher intensity signals with darker pixels than pixels used to render data points representing lower intensity signals,
      wherein the processor is further configured to filter the 3D dataset to increase a difference between signal values and noise values prior to comparing the data points of the 3D dataset to a threshold value.

13. The system of claim 12, further comprising a user interface configured to receive a user input, wherein the user input defines a threshold value; or
   defines a filter applied by the processor to filter the 3D dataset; or
   defines the volume of the 3D data set; or
   defines a feature to be included in the inverted render; or
   sets a contrast of the inverted render or an opacity of the inverted render.

* * * * *